US00PP17681P2

(12) United States Plant Patent
Iwaki et al.

(10) Patent No.: US PP17,681 P2
(45) Date of Patent: May 1, 2007

(54) ***PETUNIA* PLANT NAMED 'SUNHORE'**

(50) Latin Name: *Petunia×hybrida*
Varietal Denomination: Sunhore

(75) Inventors: Kazunari Iwaki, Shiga (JP); Kiyoshi Miyazaki, Shiga (JP); Takuro Ishihara, Tokyo (JP); Shinya Miyano, Tounosyou-machi (JP)

(73) Assignees: Keisei Rose Nurseries, Inc., Tokyo (JP); Suntory Flowers, Ltd., Tokyo (JP)

( * ) Notice: Subject to any disclaimer, the term of this patent is extended or adjusted under 35 U.S.C. 154(b) by 0 days.

(21) Appl. No.: 11/259,233

(22) Filed: Oct. 26, 2005

(51) Int. Cl.
*A01H 5/00* (2006.01)

(52) U.S. Cl. ..... Plt./356

(58) Field of Classification Search ..... Plt./356
See application file for complete search history.

*Primary Examiner*—Kent Bell
*Assistant Examiner*—June Hwu
(74) *Attorney, Agent, or Firm*—C. A. Whealy

(57) ABSTRACT

A new and distinct cultivar of *Petunia* plant named 'Sunhore', characterized by its outwardly spreading, mounded and decumbent plant habit; vigorous and freely branching growth habit; freely flowering habit; large coral pink-colored flowers with purple-colored venation; long flowering period; and good garden performance.

1 Drawing Sheet

Botanical designation: *Petunia×hybrida.*
Cultivar denomination: 'Sunhore'.

BACKGROUND OF THE INVENTION

The present Invention relates to a new and distinct cultivar of *Petunia* plant, botanically known as *Petunia×hybrida,* and hereinafter referred to by the cultivar name Sunhore.

The new *Petunia* is a naturally-occurring branch mutation of the *Petunia×hybrida* cultivar Revolution Marrose, disclosed in U.S. Plant Pat. No. 10,904. The new *Petunia* was discovered and selected by the Inventors in a controlled environment in Higashiomi, Shiga, Japan in April, 2000.

Asexual reproduction of the new cultivar by terminal cuttings in a controlled environment in Higashiomi, Shiga, Japan since October, 2000 has shown that the unique features of this new *Petunia* are stable and reproduced true to type in successive generations.

SUMMARY OF THE INVENTION

Plants of the cultivar Sunhore have not been observed under all possible environmental conditions. The phenotype may vary somewhat with variations in environment such as temperature and light intensity without, however, any variance in genotype.

The following traits have been repeatedly observed and are determined to be the unique characteristics of 'Sunhore'. These characteristics in combination distinguish 'Sunhore' as a new and distinct *Petunia* cultivar:

1. Outwardly spreading, mounded and decumbent plant habit.
2. Vigorous and freely branching growth habit.
3. Freely flowering habit.
4. Large coral pink-colored flowers with purple-colored venation.
5. Long flowering period.
6. Good garden performance.

Plants of the new *Petunia* differ from plants of the parent, the cultivar Revolution Marrose, in the following characteristics:

1. Plants of the new *Petunia* are smaller than plants of the cultivar Revolution Marrose.
2. Plants of the new *Petunia* have shorter internodes than plants of the cultivar Revolution Marrose.
3. Plants of the new *Petunia* have narrower leaves than plants of the cultivar Revolution Marrose.
4. Flower petals of plants of the new *Petunia* have more rounded apices than flower petals of plants of the cultivar Revolution Marrose.

Plants of the new *Petunia* can be compared to plants of the cultivar Revolution Brilliantpink, disclosed in U.S. Plant Pat. No. 6,914. In side-by-side comparisons conducted in Higashiomi, Shiga, Japan, plants of the new *Petunia* differed from plants of the cultivar Revolution Brilliantpink in the following characteristics:

1. Plants of the new *Petunia* were smaller than plants of the cultivar Revolution Brilliantpink.
2. Plants of the new *Petunia* had more rounded petal apices than plants of the cultivar Revolution Brilliantpink.
3. Plants of the new *Petunia* and the cultivar Revolution Brilliantpink differed in petal coloration as plants of the cultivar Revolution Brilliantpink had red purple-colored petals.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Petunia.*

The photograph at the top of the sheet comprises a side perspective view of a typical flowering plant of 'Sunhore' grown in a container.

The photograph at the bottom of the sheet comprises a close-up view of typical flowers of 'Sunhore'.

DETAILED BOTANICAL DESCRIPTION

The aforementioned photographs and following observations and measurements describe plants grown in Higashiomi, Shiga, Japan, in 15-cm containers for about four months in a polyethylene-covered greenhouse during the early spring with day temperatures about 18° C. and night temperatures about 14° C. Plants were pinched one time. Color references are made to The Royal Horticultural Society Colour Chart, 2001 Edition, except where general terms of ordinary dictionary significance are used.

Botanical classification: *Petunia×hybrida* cultivar Sunhore.

Parentage: Naturally-occurring branch mutation of the *Petunia×hybrida* cultivar Revolution Marrose, disclosed in U.S. Plant Pat. No. 10,904.

Propagation:

*Type cutting.*—Terminal vegetative cuttings.

*Time to initiate roots.*—About one week at 20° C. to 25° C.

*Time to develop roots.*—About three weeks at 20° C. to 25° C.

*Root description.*—Fine, fibrous, fleshy; light brown in color.

*Rooting habit.*—Freely branching; dense.

Plant description:

*Plant and growth habit.*—Annual flowering plant; indeterminate; outwardly spreading, mounded and decumbent plant habit. Viscid and glandular pubescent. Vigorous growth habit. Freely branching habit with lateral branches developing potentially at every node.

*Plant height.*—About 5.8 cm.

*Plant diameter.*—About 81.4 cm.

*Lateral branches.*—Length: About 45.4 cm. Diameter: About 3.9 mm. Internode length: About 1.3 cm. Texture: Pubescent. Color: 187A.

*Foliage description.*—Arrangement: Alternate, simple. Length: About 4.7 cm. Width: About 2.5 cm. Shape: Elliptic. Apex: Obtuse. Base: Cuneate. Margin: Entire; undulate. Texture, upper and lower surfaces: Pubescent; viscid. Venation pattern: Pinnate; reticulate. Color: Developing and fully expanded foliage, upper surface: 144A; venation, close to 144C. Developing and fully expanded foliage, lower surface: 144B; venation, close to 187A. Petiole length: About 2.6 mm. Petiole diameter: About 1.2 mm. Petiole texture, upper and lower surfaces: Viscid. Petiole color, upper and lower surfaces: 144C occasionally overlain with 187A.

Flower description:

*Flower type and habit.*—Single salverform flowers; flowers face mostly upward or outward; axillary. Flowers not persistent. Freely flowering habit with about 45 flowers and flower buds per plant.

*Natural flowering season.*—Long flowering period, plants flower from spring through late autumn in Japan; flowering continuous during this period.

*Flower longevity on the plant.*—About five days.

*Fragrance.*—Moderate.

*Flower size.*—Diameter: About 7.6 cm. Length: About 5.2 cm. Throat diameter (distal): About 1.7 cm. Tube diameter (proximal): About 9 mm.

*Flower buds.*—Length: About 4 cm. Diameter: About 9 mm. Shape: Cylindrical. Color: 59B; venation, N186B.

*Corolla.*—Quantity/arrangement: Five petals; fused, funnelform. Petal length: About 2.8 cm. Petal width: About 3.8 cm. Petal shape: Very broadly obovate. Petal apex: Obtuse. Petal margin: Entire; undulate. Petal texture, upper and lower surfaces: Smooth; satiny. Color: Petal, when developing, upper surface: 54A; venation, 45B or N79A. Petal, when developing, lower surface: 47C; venation, N79A. Petal, fully opened, upper surface: 55C; venation, N79A. Petal, fully opened, lower surface: 47C; venation, N79A. Flower throat (inside): 76A; venation, N79A. Flower tube (outside): 76B; venation, N79A.

*Sepals.*—Arrangement/appearance: Single whorl of five sepals fused at base, star-shaped calyx. Length: About 1.9 cm. Width: About 4.8 mm. Shape: Elliptic. Apex: Obtuse. Margin: Entire; undulate. Texture, upper and lower surfaces: Pubescent. Color, upper surface: 144B. Color, lower surface: Towards the apex, 144B; towards the base, 183A.

*Peduncles.*—Length: About 1.5 cm. Width: About 2.2 mm. Strength: Moderately strong. Texture: Pubescent; viscid. Color: 184A.

*Reproductive organs.*—Stamens: Quantity: Five per flower. Anther shape: Ellipsoidal. Anther length: About 1.8 mm. Anther color: 77A. Pollen amount: Scarce. Pollen color: 90B. Pistils: Quantity: One per flower. Pistil length: About 1.8 cm. Style length: About 1.4 cm. Style color: 144A. Stigma shape: Ellipsoidal. Stigma color: 144D. Ovary color: 144C.

*Seeds.*—Seed development has not been observed.

Disease/pest resistance: Plants of the new *Petunia* have not been noted to be resistant to specific pathogens and pests common to *Petunia*.

Garden performance: Plants of the new *Petunia* have been observed to have good garden performance and tolerate rain, wind and tolerated temperatures from 0° to 35° C.

It is claimed:

1. A new and distinct cultivar of *Petunia* plant named 'Sunhore', as illustrated and described.

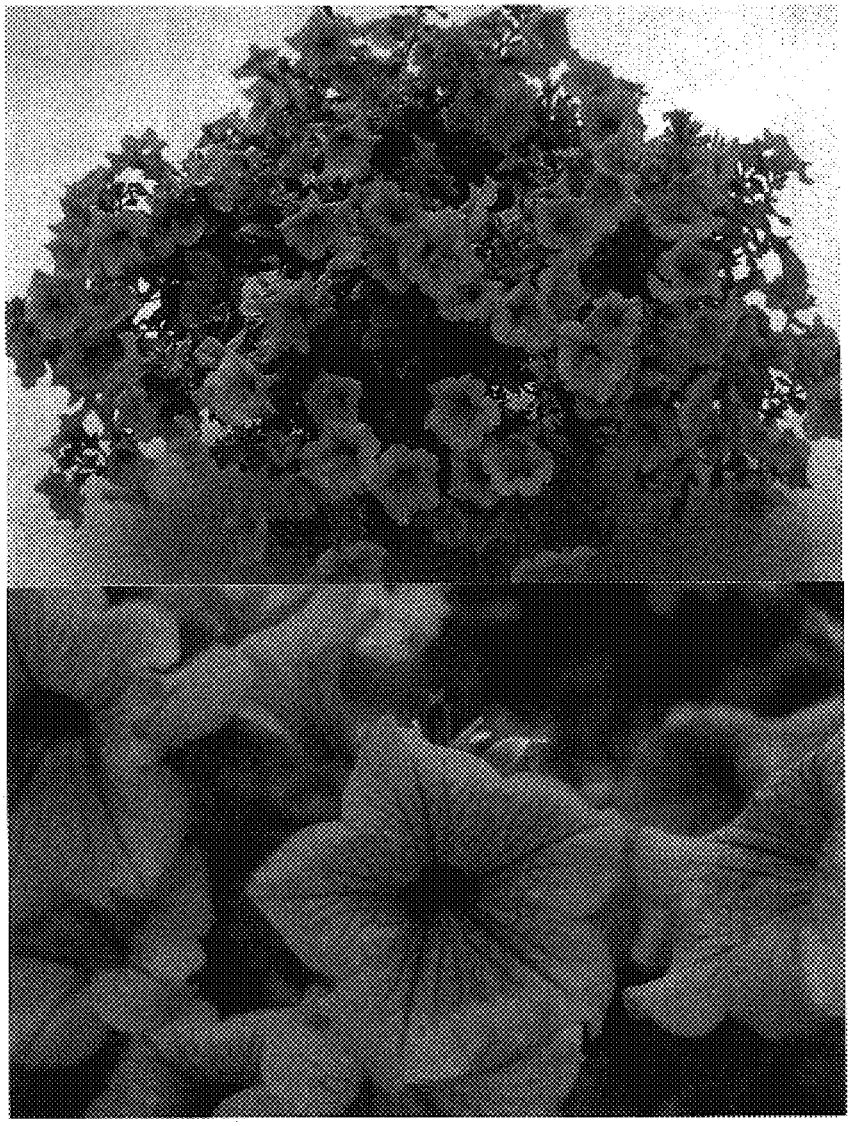

* * * * *